United States Patent
Akubuike

(10) Patent No.: US 11,351,216 B2
(45) Date of Patent: Jun. 7, 2022

(54) ANXIETY MANAGEMENT SUPPLEMENT

(71) Applicant: Ngozichukwu Akubuike, Saint Paul, MN (US)

(72) Inventor: Ngozichukwu Akubuike, Saint Paul, MN (US)

( * ) Notice: Subject to any disclaimer, the term of this patent is extended or adjusted under 35 U.S.C. 154(b) by 133 days.

(21) Appl. No.: 16/941,108

(22) Filed: Jul. 28, 2020

(65) Prior Publication Data

US 2022/0031786 A1    Feb. 3, 2022

(51) Int. Cl.
| | |
|---|---|
| *A61K 36/00* | (2006.01) |
| *A61K 36/38* | (2006.01) |
| *A61K 36/185* | (2006.01) |
| *A61K 9/107* | (2006.01) |
| *A61P 25/22* | (2006.01) |
| *A61K 35/644* | (2015.01) |
| *A61K 47/36* | (2006.01) |
| *A61K 9/06* | (2006.01) |

(52) U.S. Cl.
CPC ............ *A61K 36/38* (2013.01); *A61K 9/06* (2013.01); *A61K 9/107* (2013.01); *A61K 35/644* (2013.01); *A61K 36/185* (2013.01); *A61K 47/36* (2013.01); *A61P 25/22* (2018.01)

(58) Field of Classification Search
None
See application file for complete search history.

(56) References Cited

FOREIGN PATENT DOCUMENTS

KR    2015066187 A    *    6/2015

* cited by examiner

*Primary Examiner* — Michael V Meller
(74) *Attorney, Agent, or Firm* — Essen Law Office, PLLC

(57) ABSTRACT

A composition of phyto-medicaments comprising essentially of *Garcinia kola*, pomegranate and *Moringa oleifera* for the treatment necessary to alleviate anxiety, ailments associated therewith.

1 Claim, No Drawings

ANXIETY MANAGEMENT SUPPLEMENT

BACKGROUND

People who suffer from persistent sinus infection, nagging health issues such as stress and anxiety, including depression can attest to the challenges and desperation in getting or obtaining treatment for their ailments without the rigor of suffering with adverse effects of the medicaments that they have to take. It is also an issue of concern that almost all the medicament taken or consumed by these patients present yet again foreign material or abstracts into them. The prevalence of non-botanical medication for anxiety and related issues with their attendant side effects have become sources of concern and trepidation for people suffering from these ailments, just as examples.

Nutraceuticals and other pharmaceuticals may present medicaments that come with issues of potency and sourcing. Potency, in that nutraceuticals are from sources that may affect the efficacy of the medicament caused by the quality of the raw materials used. Biologics offer some solutions to sufferers and there is recognition that biologics that are without careful processing may provide challenges because of the additives that make them usable for their intended purpose or purposes.

Drugs, and other non-homeopathic formulations or similarly fabricated medicines used to treat issues of anxiety, hypertension or weight management, among others are typically tied to some adverse effects of such treatment. It is thus reasonable to imagine patients who would rather suffer than take medication that would cause them more challenges than those they already know and manage.

It is commonly agreed that the when someone ails with anxiety or depression, the likelihood of weight gain is high. These issues make especially arduous, the ability to address one ailment wrapped up in the other ailments that a person has to deal with.

From the foregoing and more, it will be appreciated that what is needed in the art is a formulation that provides some relief to sufferers of anxiety, weight gain, body aches and pains and related challenges that is devoid of the attendant adverse effects. Such system is disclosed and claimed herein.

SUMMARY

In one embodiment, the present invention provides a combination of phyto-medicaments comprising essentially of *Piper guineense*, turmeric and *Moringa oleifera* for the treatment necessary to alleviate ailments associated therewith.

In another embodiment of the present invention, the phyto-medicament composition consists of *Piper guineense*, *Moringa oleifera*, turmeric and ginger formulated for the purpose of providing relief to patients of aches and ailments of the related to inflammation of the nerves.

The composition of the present invention may preferably include the aforesaid phyto-medicament with additives, such as aromatic olive oils, *Cinnamomum verum*, honey and minerals.

DETAILED DESCRIPTION

The present invention provides a composition of phyto-medicaments, uniquely formulated for the relief of anxiety, body aches, and inflammation challenges including, and not limited to those useful for the treatment of body aches, agues, inflammations, high blood pressure and weight management and other such challenges that may include stomach churns and similar aches that affect a large population of folks, in some cases, after food intake or consumption of medications The present invention comprises *Garcinia kola*, and *Moringa oleifera* and, in some optional circumstance, corn starch and further optionally, white honey. In some instances, the formulation of the present invention includes pomegranate. The present invention comprises *Garcinia kola*, sometimes referred to as bitter kola, said *Garcinia kola* preferably being available skinned off for use in the instant formulation. Given the prevalence of *Garcinia kola* in many parts of the world, preferable origin of the usable form of *Garcinia kola* is a tropically and organically grown variety from West Africa. The version of the *Garcinia kola* usable in the present invention are preferably dry to between about 20 to 50 percent moisture content. In some instances, wherein the *Garcinia kola* presents with more moisture content, air drying the *Garcinia kola* after chopping into pieces might be useful to attain textural quality for grinding or blending into a paste. Further processing of the *Garcinia kola* into ground paste may including pounding in a mortar and pestle of blending using available blenders, preferably Nutribullet brand available from Nutribullet Company of Los Angeles, Calif. Useful amount for formulation of the present invention include preferably between about 1 and 3 teaspoonfuls; more preferably between about 1 and 2.5 teaspoonfuls and most preferably between about 1 and 2 teaspoonfuls of *Garcinia kola* per formulation.

The *Moringa oleifera* usable in the instant disclosure may be in the form of leaves. *Moringa* leaves usable in the present invention are preferably collected and air-dried. The dried leaves are preferably blended prior to further blending or combination with other components of the present invention. *Moringa oleifera* leaves are most usable as normal green leaves and prior to any discoloration which my signify loss of chlorophyll or diminution in quality. Ground *Moringa oleifera* usable is about one cup (8 ounces) per formulation according to the present invention.

When and where used, the present invention optionally includes pomegranate. Pomegranate, usable in the present invention is preferably usable in the form of powder. Pomegranate powder may be prepared by removing the skin and juicing the seeds, then freeze drying the juice into powder. This process ascertains the quality of the pomegranate for preferable use in the present invention. Preparation of the pomegranate powder from juicing and freeze drying may preferably be accomplished using blenders such as Nutribullet blenders to operably produce the juicing of the seeds. Alternatively, pomegranate powder commercially available may be obtained from Navitas Organics in Novato, Calif. An amount usable for the present invention may be between about 1 measured cup (8 ounces) and about 1.5 measured cups (12 ounces) of pomegranate powder.

Optionally, the present invention may also include corn starch. Corn starch is preferentially gluten free, and commonly available. Commercial brand of cornstarch usable in the present invention is Argo® and may be obtained from any grocery store. Preferable amount of cornstarch usable is about 1 teaspoonful in about 8 ounces of the formulation of the present invention.

The present invention may also include water (preferably purified) and honey to suitable taste, texture and composition. Honey usable in the present invention is preferably white honey. White honey provides antioxidant properties and may typically be creamy, less sweet and less syrupy. It is notable that the honey may be adapted to by less syrupy by providing warmth or such temperature fluctuation as deemed appropriate to obtain a suitable texture for use. In its natural state, white honey possesses these qualities that extra activities are preferably unnecessary to attain the needed quality for use.

The present invention may also useful for the prevention or management of weight, bowel movements, blood pressure, glucose control or some measure of anxiety reduction and more. While these are subject to future testimonials, user experience and results support efficacies in these areas. In use, the present invention may be blended, and imbibed in 2 tablespoonfuls (0.33 oz) per 8 ounces of hot water.

There may be other non-essential adjuvants that may be included as production demands for the preservation, availability, appeal, taste or other such attributes without affecting the efficacy or functionality of the composition of the present invention.

Example I

A composition comprising about 1 cup (8 ounces) of *Moringa oleifera*, 1 teaspoonful of *Garcinia kola*, 1 teaspoonful of pomegranate, less than 1 teaspoonful of white honey; all blended to a paste. The paste was thereafter used as a base formulation and 2 tablespoonfuls stirred in an 8 ounce of hot water. Same dosage was provided for relief from high blood pressure on a regular bases of each morning and night. A person who presented with anxiety saw relief after 2 weeks of use of the present invention

Having thus described the preferred embodiments of the present invention, those of skill in the art will readily appreciate that the teachings found herein may be applied to yet other embodiments within the scope of the claims hereto attached. The complete disclosure of all patents, patent documents, and publications are incorporated herein by reference as if individually incorporated.

What is claimed:

1. An emulsion consisting essentially of *Garcinia kola* extract, *Moringa oleifera* extract, honey, pomegranate extract, corn starch and *Piper guineense* extract.

* * * * *